(12) United States Patent
Ellis et al.

(10) Patent No.: US 6,653,607 B2
(45) Date of Patent: Nov. 25, 2003

(54) HEATING PAD SYSTEMS, SUCH AS FOR PATIENT WARMING APPLICATIONS

(75) Inventors: Kent Douglas Ellis, Seattle, WA (US); Charles C. Wyatt, Laguna Woods, CA (US)

(73) Assignee: American Healthcare Products, Inc., Redmond, WA (US)

( * ) Notice: Subject to any disclaimer, the term of this patent is extended or adjusted under 35 U.S.C. 154(b) by 73 days.

(21) Appl. No.: 09/880,725

(22) Filed: Jun. 12, 2001

(65) Prior Publication Data

US 2002/0019654 A1 Feb. 14, 2002

Related U.S. Application Data

(60) Provisional application No. 60/212,380, filed on Jun. 14, 2000.

(51) Int. Cl.[7] .......................... H05B 3/00; A61G 13/00
(52) U.S. Cl. .................... 219/528; 219/521; 219/217; 219/218; 219/212; 5/421; 607/96
(58) Field of Search ....................... 219/528, 529, 219/549, 521, 218, 212, 217; 5/421, 690, 600, 603; 607/96, 112, 98

(56) References Cited

U.S. PATENT DOCUMENTS

| | | | |
|---|---|---|---|
| 2,688,070 A | | 8/1954 | Freedlander |
| 3,423,574 A | * | 1/1969 | Shomphe et al. ............ 219/528 |
| 3,553,749 A | * | 1/1971 | Majeske ........................ 5/690 |
| 3,900,654 A | * | 8/1975 | Stinger ........................ 219/213 |
| 4,310,745 A | * | 1/1982 | Bender ........................ 219/213 |
| 4,423,308 A | * | 12/1983 | Callaway et al. ............ 219/217 |
| 4,788,417 A | * | 11/1988 | Graflind ...................... 219/528 |
| 4,833,305 A | | 5/1989 | Mashimo et al. |
| 5,031,261 A | * | 7/1991 | Fenner, Sr. ..................... 5/736 |
| 5,138,138 A | * | 8/1992 | Theilacker et al. ......... 219/218 |
| 5,265,296 A | * | 11/1993 | Abbas et al. ................ 219/528 |
| 5,324,911 A | * | 6/1994 | Cranston et al. ............ 219/218 |
| 5,371,340 A | * | 12/1994 | Stanfield ...................... 219/528 |
| 5,385,529 A | * | 1/1995 | Koch ............................ 600/22 |
| 5,451,747 A | * | 9/1995 | Sullivan et al. .............. 219/528 |
| 5,494,051 A | * | 2/1996 | Schneider, Sr. .............. 128/870 |
| 5,516,189 A | * | 5/1996 | Ligeras .................... 297/180.11 |
| 5,604,021 A | * | 2/1997 | Wagner .......................... 5/736 |
| 5,720,774 A | * | 2/1998 | Glucksman ................... 607/96 |
| 5,785,716 A | * | 7/1998 | Bayron et al. ............... 607/108 |
| 5,881,410 A | * | 3/1999 | Yamada .......................... 5/713 |
| 5,932,129 A | | 8/1999 | Hyatt |
| 5,948,303 A | * | 9/1999 | Larson .......................... 5/421 |
| 6,006,136 A | | 12/1999 | Glucksman |

FOREIGN PATENT DOCUMENTS

| | | | |
|---|---|---|---|
| CA | 969621 | * | 6/1975 |
| DE | 2308214 A | | 8/1974 |
| DE | 3405425 | * | 8/1985 |
| DE | 3707948 A | | 9/1988 |
| DE | 29809445 | * | 8/1998 |
| EP | 677283 | * | 10/1995 |
| EP | 757 907 | | 2/1997 |
| GB | 2255262 | * | 10/1992 |
| JP | 57-180888 | * | 11/1982 |
| JP | 57-180888 A | | 11/1982 |
| JP | 2-276185 | * | 11/1990 |
| JP | 3-165746 | * | 7/1991 |
| JP | 4-73883 | * | 3/1992 |
| JP | 10-43258 A | | 2/1998 |
| JP | 11-214131 | * | 8/1999 |
| JP | 2001238924 | * | 9/2001 |

\* cited by examiner

*Primary Examiner*—John A. Jeffery
(74) *Attorney, Agent, or Firm*—Perkins Coie LLP

(57) ABSTRACT

A heating pad system is useable in one embodiment for warming a person on a support structure. In this embodiment, the heating pad system comprises an upper foam pad, a lower foam pad, and a thermal-electric heating element sandwiched between the upper and lower foam pads. A form-fitting waterproof cover encloses at least a portion of the upper and lower foam pads and the thermal-electric heating element. In one aspect of this embodiment, the heating pad system includes a power unit for providing electrical power to the thermal-electric heating element, the power unit including a control panel having at least one temperature selector, the temperature selector for selecting at least one heating pad temperature.

65 Claims, 10 Drawing Sheets

HEATING PAD SYSTEMS, SUCH AS FOR PATIENT WARMING APPLICATIONS

CROSS-REFERENCE TO RELATED APPLICATION

This application claims the benefit of U.S. Provisional Application No. 60/212,380, filed Jun. 14, 2000, currently pending and incorporated herein by reference.

TECHNICAL FIELD

Embodiments described herein related generally to heating pad systems, such as heating pad systems useable for warming patients during ambulance transport or hospital procedures.

BACKGROUND

Patient warming is a significant concern in many medical situations. In emergency rooms, for example, many of the trauma patients admitted are hypothermic. If their hypothermia is not addressed, these patients can go into shock. Similarly, in hospitals, some adult patients will experience hypothermia during or after surgery. If prolonged, the detrimental physiological consequences of this hypothermia represents a significant risk to these surgical patients.

Hypothermia reduces the blood flow to the appendages of the body in order to protect the vital organs. It is a natural defense mechanism that can only be treated by warming the patient. Studies have shown that such hypothermia may be related to the development of serious postoperative complications, such as impaired platelet function and increased blood loss, resulting in heightened transfusion requirements.

Conventional methods for preventing intraoperative temperature decline in surgical patients include pre-warming a blanket using a blanket warming device and then placing the warmed blanket over the patient. A convection heating device is also available that blows heated air through a duct into a nonwoven blanket placed over the patient. The nonwoven blanket has channels for the heated air to circulate in and is disposable, making cleaning unnecessary. Another product circulates heated water through a blanket in a similar manner. This water filled device, however, is typically placed under the patient.

Known methods such as these for preventing temperature decline are often inefficient and ineffective, particularly in older patients. Convection heating devices, for example, have proven expensive because of the disposable nonwoven blankets, not to mention the energy and maintenance requirements. The high temperatures of the heated air duct in close proximity to anesthetized patients has also raised concerns. In addition, like pre-warmed blankets placed over the patient, they warm the patient inefficiently from above, which has the collateral negative effect of limiting clinical access to the patient from the topside. Both the air and water devices require relatively large amounts of energy, noisy pumps, and significant maintenance in the clinical environment. In light of the shortcomings associated with conventional patient warming devices, a low maintenance patient warming device that efficiently warms a patient to a desired temperature, uses little energy, avoids high temperatures, and overcomes other problems would be desirable.

Figure 1:
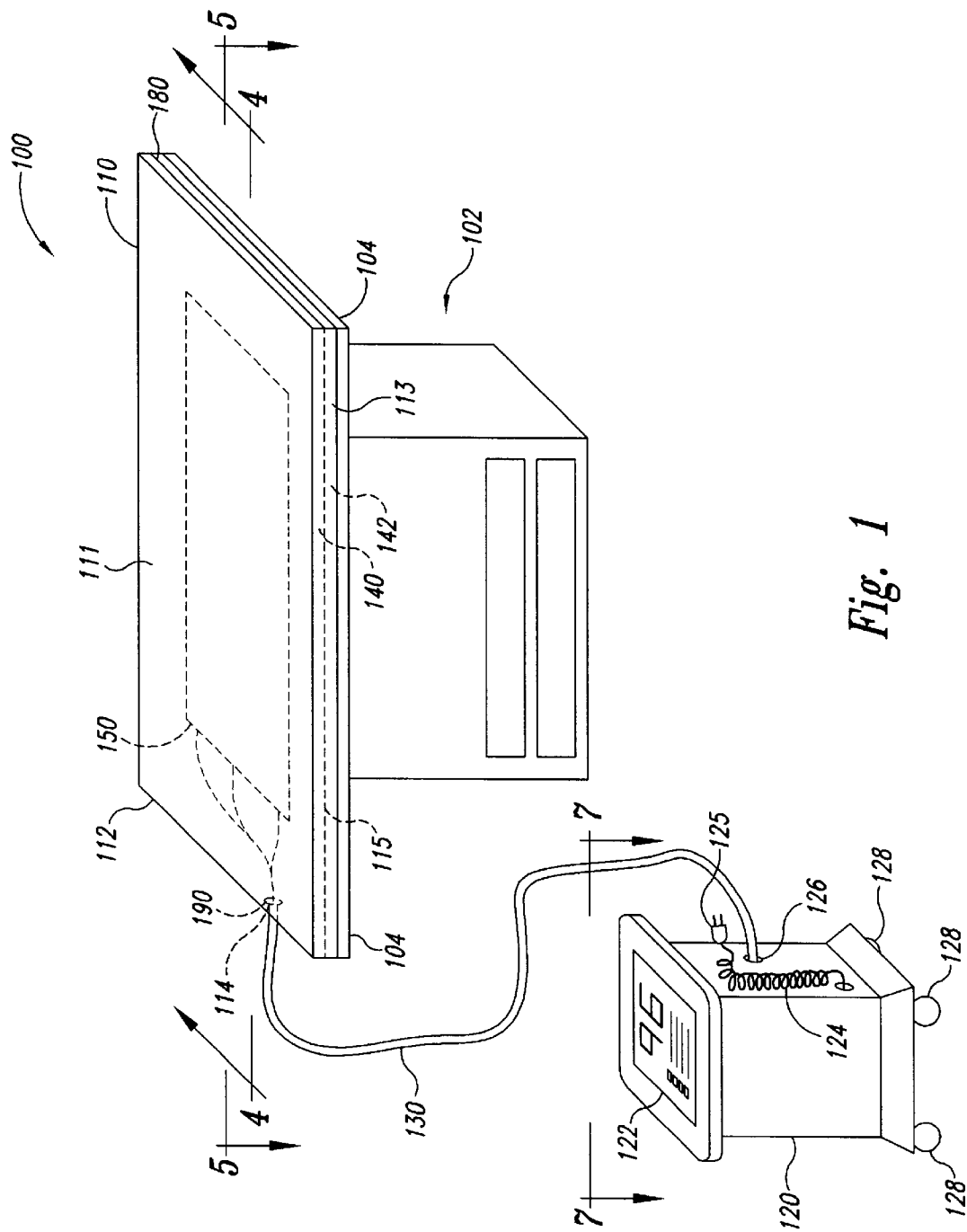
FIG. 1 is an isometric view of a heating pad system in accordance with an embodiment of the invention.

In the drawings, the same reference numbers identify identical or substantially similar elements or acts. To easily identify the discussion of any particular element or act, the most significant digit or digits in a reference number refer to the Figure number in which that element is first introduced (e.g., element 1104 is first introduced and discussed with respect to FIG. 11).

DETAILED DESCRIPTION

The following disclosure describes heating pad systems useable for personal warming in a number of different settings. In one embodiment, a heating pad system includes a heating pad that can be used for warming patients during various hospital procedures. For example, the heating pad of this embodiment can be used to warm a patient during ambulance or gurney transport, during operating room procedures, or during post-operative recuperation. In another embodiment, a heating pad system includes two heating pads hingedly connected together that can be positioned on the seat and back portions of a chair or other seating device to warm a person situated on the seating device. The heated pads of this embodiment may find particular utility warming sitting patients undergoing kidney dialysis treatment whose body temperatures tend to drop as a result of cooled blood reentering their bodies.

Many specific details of certain embodiments of the invention are set forth in the following description and figures to provide a thorough understanding of, and an enabling description for, such embodiments. One of ordinary skill in the relevant art, however, will understand that the present invention may have additional embodiments, or that the invention may be practiced without several of the details described in the following disclosure. In other instances, structures and functions that are well known to those of ordinary skill in the relevant art have not been shown or described in detail herein to avoid unnecessarily obscuring the description of embodiments of the invention.

FIG. 1 is an isometric view of a heating pad system 100 in accordance with an embodiment of the invention. The heating pad system 100 of the illustrated embodiment is an operating room (OR) table heating pad system that includes a rectangular-shaped heating pad 110 positioned on a stationary support structure 102, such as a conventional OR table. The heating pad system 100 also includes a power unit 120 that is freestanding and provides electrical power to, and receives temperature data from, the heating pad 110 through a utility cord 130. In alternate embodiments, the power unit is secured to or integral with the OR table.

In one aspect of this embodiment, the heating pad 110 is comprised of an upper pressure relief foam pad 140, a lower pressure relief foam pad 142, and a heating element 150 sandwiched therebetween. The upper and lower foam pads 140 and 142 and the heating element 150 are enclosed within a form-fitting waterproof and antimicrobial cover 112 that seals the foam against moisture and other contaminants. In the illustrated embodiment, the cover 112 includes a top portion 111 and a bottom portion 113 that are joined together along a pad perimeter 115 with welded or sealed seams to prevent fluid ingress and contamination. In another aspect of this embodiment, a sealable closing device 180, such as a spiral zipper, can be provided toward one end of the heating pad 110 to allow access to the interior of the cover 112 for removal or maintenance of the foam pads 140 and 142 or the heating element 150. In an alternate embodiment, this closing device can be omitted and the heating pad 110 can be a closed unit. The heating pad 110 is vented in one embodiment through a vent tube 190 that sealably passes from the interior of the cover 112 through a sealed connector 114 located toward one end of the heating pad 110. The vent tube 190 is incorporated into the utility cord 130 and vents into the power unit 120. In an alternate embodiment, the vent tube 190 can be omitted and a vent filter can be incorporated into the cover 112 for venting the heating pad 110.

The electrical power for the heating element 150 enters the cover 112 through the sealed connector 114. In one aspect of this embodiment, the sealed connector 114 is a tortuous-path connector that prevents ingress of fluids and other contaminants inside the cover 112 by providing a tortuous path that fluids and contaminants cannot breach. A receptacle 126 connects the utility cord 130 to the power unit 120. In another aspect of this embodiment, the receptacle 126 is a sealed locking DIN connector for preventing accidental disconnection of the utility cord 130 from the power unit 120. In other embodiments, other connectors, such as nonlocking connectors, can be used, or alternatively the utility cord 130 can simply be hard-wired into the power unit 120.

The power unit 120 has a control panel 122 that includes temperature controls and information displays for the heating pad system 100. In one aspect of this embodiment, the control panel 122 is a top-facing control panel that provides a horizontal interface that can be easily seen and reached by hospital personnel working around the OR table. The freestanding power unit 120 also includes a plurality of casters 128 rotatably attached to its underside for mobility. This mobility enables the power unit 120 to be neatly stowed underneath an overhanging portion 104 of the stationary support structure 102 to avoid interference with hospital personnel (not shown) working around the stationary support structure. A retractable power cord 124 is included on the power unit 120 for connecting the power unit to an external power source, such as an AC outlet in the OR facility. In one aspect of this embodiment, the retractable power cord 124 includes a three-prong plug 125, such as a standard hospital grade NEMA 15 three-prong plug, for making the connection to the external power source.

The heating pad system 100 can be used in accordance with an embodiment of the invention to provide efficient warmth and uniformly distributed support to a patient (not shown) situated on the heating pad 110 during an OR procedure. For example, after connecting the power unit 120 to a suitable AC power source, hospital personnel can select an appropriate pad temperature on the control panel 122 based on the type of procedure planned for the patient or the existing thermal condition of the patient. The pad will accordingly come up to the selected temperature momentarily and begin to warm the patient. Alternatively, the patient can be placed on the heating pad 110 after the pad temperature is selected and the pad has come up to temperature. Accordingly, the heating pad 110 will generate heat as required to maintain the surface of the pad at the selected temperature, thereby efficiently and comprehensively warming the patient to a favorable temperature and reducing the likelihood of medical complications arising from a drop in the patient's body temperature.

One advantage of the heating pad system 100 over conventional warming devices that warm the patient from the topside, such as pre-warmed topical blankets, is that the heat is more efficiently applied to the patient's body through the comprehensive foam support provided beneath the patient. Pre-warmed blankets placed over the patient waste thermal energy that rises upward off these blankets away from the patient. In contrast, the heating pad of the present invention is positioned beneath the patient so that thermal energy rising off the heating pad will naturally be absorbed by the patient and not wasted. A further advantage of the present invention is that it affords hospital personnel complete access to the patient without compromising patient warmth.

The present invention also provides the advantage of reducing the likelihood of bedsores. Bedsores, once thought only to occur after long periods in a conventional bed, can also occur as a result of long OR procedures on surfaces that lack the pressure relief foam of this embodiment. On some conventional OR tables, the patient is often supported on localized pressure points. In contrast, the increased contact area provided by the pressure relief foam provides comprehensive and uniformly distributed support to the patient, avoiding maladies such as bedsores and enhancing the heat transfer properties between the heating pad and the patient.

Figure 2:
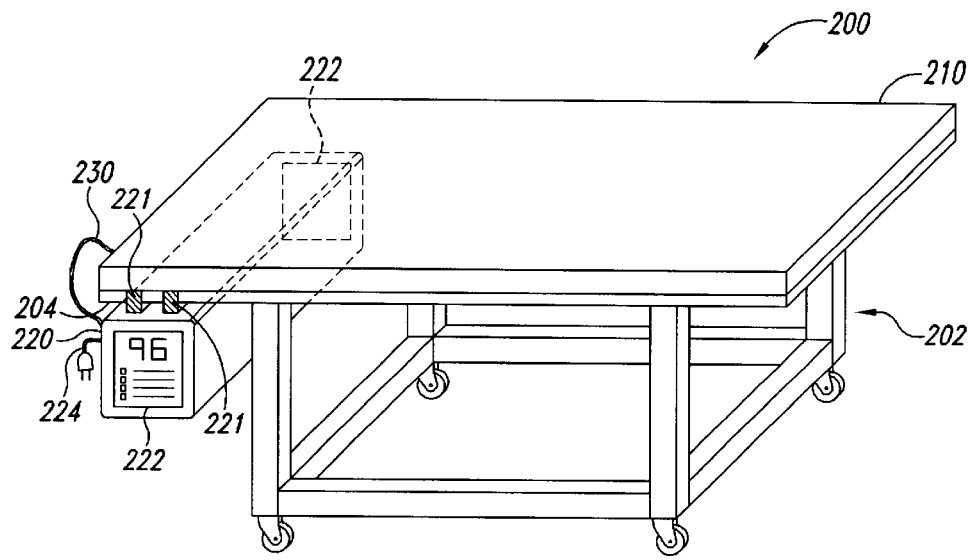
FIG. 2 is an isometric view of a heating pad system in accordance with another embodiment of the invention.

FIG. 2 is an isometric view of a heating pad system 200 in accordance with another embodiment of the invention. The heating pad system 200 of the illustrated embodiment is a gurney heating pad system that includes a rectangular-shaped heating pad 210 positioned on top of a mobile support structure 202, such as a conventional hospital gurney. In one aspect of this embodiment, the heating pad 210 is substantially similar in both structure and function as the heating pad 110 shown in FIG. 1. The heating pad system 200 also includes a portable power unit 220 for providing electrical power to, and receiving temperature data from, the heating pad 210 through a utility cord 230.

The power unit 220 includes one or more supports 221, such as support straps, for releasably suspending the power unit neatly beneath an overhanging portion 204 of the mobile support structure 202 so that it is out of the way of hospital personnel (not shown) moving or otherwise working around the mobile support structure. The power unit 220 also includes dual control panels 222 located on opposite ends of the power unit. The control panels 222 of the illustrated embodiment are side-facing and include redundant left and right side temperature controls and information displays for the heating pad 210.

In one aspect of this embodiment, the power unit 220 is a portable self-contained power unit that includes a power source, such as a storage battery. In one embodiment, this power source can be an internal storage battery. In other embodiments, this power source can be a storage battery that is mounted to the outside of the power unit 220 or is otherwise operably coupled to the power unit. This power source enables the power unit 220 to independently provide electrical power to the heating pad 210 without connecting to an external AC power source, such as a facility outlet. This enables the heating pad system 200 to provide comprehensive patient warmth regardless of the location of the mobile support structure 202 and even when the mobile support structure is being moved between locations. The power unit 220 does include, however, a retractable power cord 224 that can optionally be used to access power from an external AC power source, such as a facility outlet, if desired to operate the heating pad 210 or to recharge the internal power source.

In another aspect of this embodiment, the control panels 222 include a display that indicates the status of the power unit's internal power source. In one embodiment, this display is a visual warning device, such as a warning light, that flashes or otherwise changes its appearance when the internal power source is approaching a pre-selected power level that may compromise the continued performance of the heating pad 210. In another embodiment, this display is a digital display that graphically indicates the amount of time left on the internal power source in hours. In yet another embodiment, the control panels 222 can include an audio warning device, such as a buzzer, that sounds when the internal power source is approaching a pre-selected power level. In one aspect of this embodiment, the audio warning device can provide two or more different sounds, for example a high note and a low note, to signify different levels of stored internal power. The low note can correspond to a moderate depletion of internal power, while the high note can be reserved for a significant depletion of internal power.

The heating pad system 200 can be used in accordance with an embodiment of the invention to efficiently warm a patient (not shown) while situated on the heating pad 210 on a gurney or other similar device. For example, a trauma patient entering an emergency room, or a hospital patient being transported from a hospital room to an operating room, may spend a considerable amount of time on a gurney prior to, or in lieu of, placement on a conventional OR table. In this situation, the patient can be placed on the beating pad system 200 and hospital personnel (not shown) can select an appropriate heating pad temperature on one of the control panels 222. The heating pad 210 will then warm the patient at this selected temperature during the entire period the patient resides on the heating pad, whether for a short period during relocation or a relatively long period during surgery.

The heating pad system 200 provides the advantage of employing the self-contained power unit 220 that enables continuous patient warming even though the heating pad system 200 may not be near an AC outlet. The heating pad system 200 provides the further advantage of having dual control panels 222 facing in opposite directions. These dual control panels 222 ensure that hospital personnel will always have ready visual and tactile access to a control panel, even if one side of the mobile support structure 202 is parked against a wall, as is often the case in hospitals.

Figure 3:
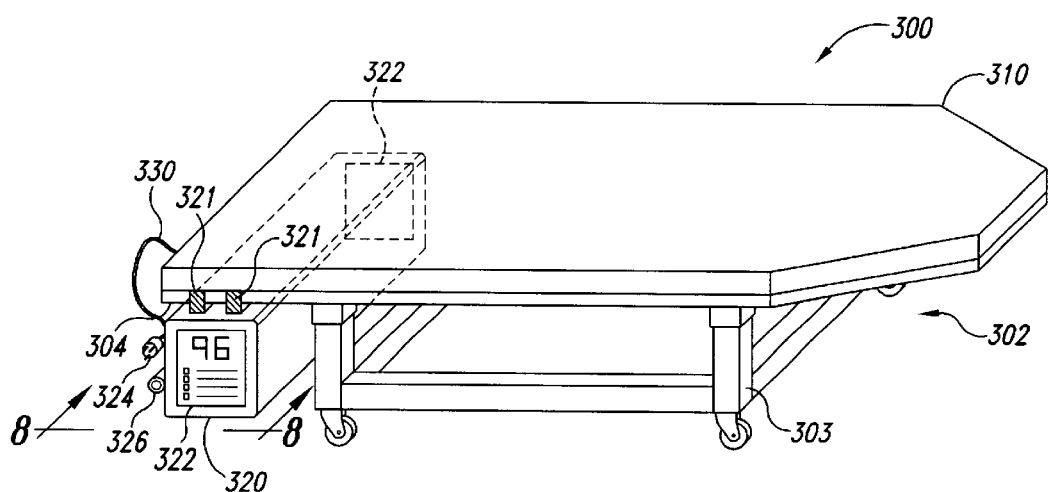
FIG. 3 is an isometric view of a heating pad system in accordance with yet another embodiment of the invention.

FIG. 3 is an isometric view of a heating pad system 300 in accordance with yet another embodiment of the invention. The heating pad system 300 of the illustrated embodiment is an ambulance gurney heating pad system that includes a shaped heating pad 310 positioned on top of a mobile support structure 302, such as a conventional ambulance gurney. The mobile support structure 302 has a collapsible undercarriage 303 for reducing the overall height of the mobile support structure. The collapsible undercarriage 303 is illustrated in FIG. 3 in a collapsed configuration, such as would be employed for transporting the mobile support structure 302 in a conventional ambulance where space is typically limited. In one aspect of this embodiment, the heating pad 310 is substantially similar both in structure and function as the heating pads 110 and 210 shown in FIGS. 1 and 2, respectively. Additionally, the front of the heating pad 310 can have a tapered shape as shown if it enhances the utility of the heating pad in ambulance applications. The heating pad system 300 also includes a portable power unit 320 for providing electrical power to, and receiving temperature data from, the heating pad 310 through a utility cord 330.

In one aspect of this embodiment, the power unit 320 can be neatly and releasably stowed underneath an overhanging portion 304 of the mobile support structure 302 using one or more supports 321, such as support straps. Stowing the power unit 320 avoids interference with paramedics or other personnel (not shown) moving or otherwise working around the mobile support structure. The power unit 320 can also be hand-carried while moving the mobile support structure 302, or mounted to an adjacent structure during ambulance transport. Like the power unit 220 of FIG. 2, the power unit 320 includes dual side-facing control panels 322 that afford easy visual and tactile access from either side of the mobile support structure 302. In one aspect of this embodiment, the control panels 322 are substantially similar both in structure and function as the control panels 222 shown in FIG. 2; however, the control panels 322 of the illustrated embodiment can be lower profile to accommodate the reduced space underneath the mobile support structure 302.

In another aspect of this embodiment, the power unit 320 is a portable self-contained power unit that includes an internal power source, such as an internal storage battery. This internal power source enables the power unit 320 to independently provide electrical power to the heating pad 310 without connecting to an external AC power source, such as a facility outlet. This enables the heating pad system 300 to provide comprehensive patient warmth regardless of location. The power unit 320, however, also includes suitable attachments for connecting to external power sources when available and when desired to operate the heating pad 310 or recharge the internal power source. For example, the power unit 320 includes a retractable power cord 324 having a conventional three-prong connector for connecting the power unit to a suitable AC electrical outlet. The power unit 320 also includes a retractable auxiliary power cord 326 for connecting to a suitable 12-volt DC power source, such as a 12-volt DC electrical power system typically found in conventional ambulances and other vehicles.

In another aspect of this embodiment that is similar to the power unit 220 discussed above, the control panels 322 include a display that indicates the status of the power unit's internal power source. In one embodiment, this display is a visual warning device, such as a warning light, that flashes or otherwise changes its appearance when the internal power source is approaching a pre-selected power level that may compromise the continued performance of the heating pad 310. In another embodiment, this display is a digital display that graphically indicates the amount of time left on the internal power source in hours. In yet another embodiment, the control panels 322 can include an audio warning device, such as a buzzer, that sounds when the internal power source is approaching a pre-selected power level.

The heating pad system 300 can be used in accordance with an embodiment of the invention to provide warmth and uniformly distributed support to a patient (not shown) situated on the heating pad 310 during transport in a conventional ambulance (also not shown), or other medical evacuation vehicle, such as a helicopter. For example, a trauma patient at an accident scene can be placed on the heating pad 310 for transport to an ambulance or other medical rescue vehicle. The undercarriage 303 can be collapsed in this situation to make the heating pad system 300 more like a conventional stretcher if this facilitates usage. A paramedic or other user can then select an appropriate heating pad temperature on one of the control panels 322 based on the physiological needs of the patient or the ambient temperature. The patient can then be transported on the heating pad system 300 to the ambulance or other such vehicle. If the undercarriage 303 is not already collapsed to the low-profile configuration, it can be collapsed before loading the heating pad system 300 into the vehicle. Once inside the vehicle, a paramedic or other user has a choice of power sources for the heating pad 310. For example, the user could elect to keep powering the heating pad 310 with the self-contained internal power source of the power unit 320, or the user could elect to power the heating pad with an external source such as a suitable 12-volt DC outlet provided by the vehicle's electrical system.

Figure 4:
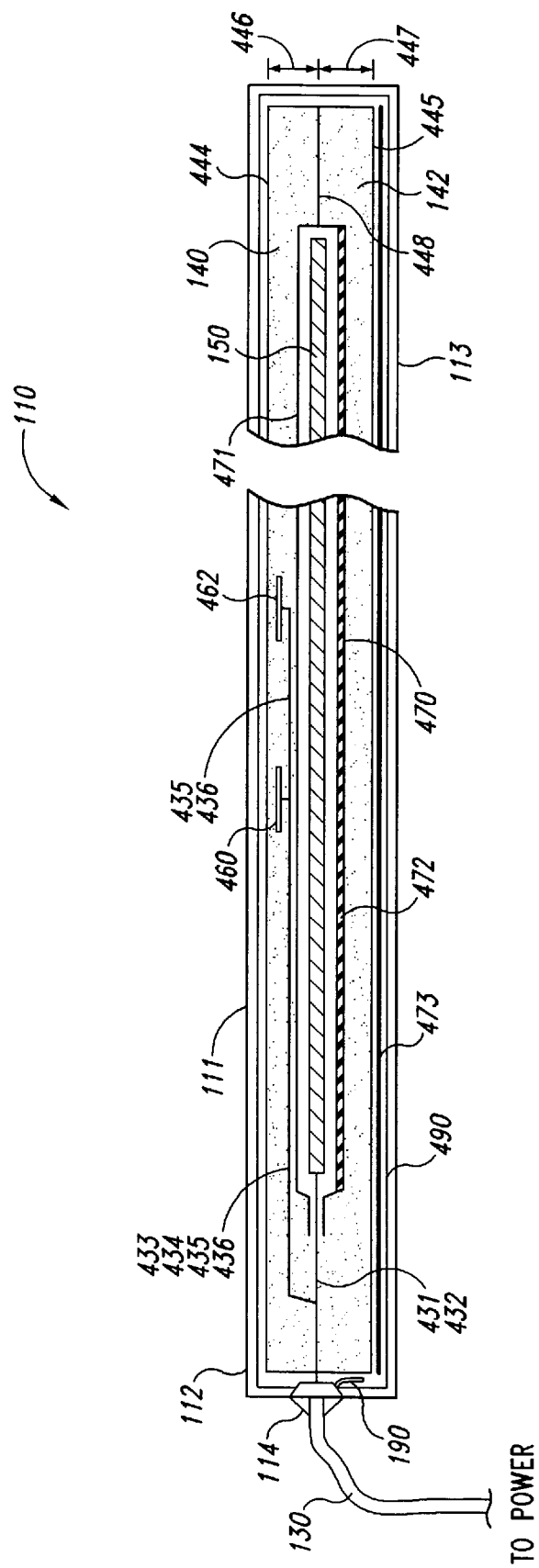
FIG. 4 is an enlarged schematic side cross-sectional view of a heating pad taken substantially along line 4—4 of FIG. 1 in accordance with an embodiment of the invention.

FIG. 4 is an enlarged schematic side cross-sectional view of the heating pad 110 taken substantially along line 4—4 of FIG. 1 in accordance with an embodiment of the invention. As mentioned above, the heating pad 110 includes the upper foam pad 140, the lower foam pad 142, and the heating element 150 sandwiched therebetween. An adhesive 448, such as a nonflammable N-Propylbromide solvent-based nonlatex spray glue, can be used between the upper and lower foam pads 140 and 142 to bond the foam pads together around a portion of the heating element 150. Power lines 431 and 432, extending from the sealed connector 114, complete the necessary electrical circuit between the power unit 120 (not shown) and the heating element 150. A temperature control sensor 460 and a temperature monitor sensor 462 are embedded in the upper foam pad 140 adjacent to an upper surface 444 of the upper foam pad. Instrumentation lines 433 and 434 extending from the sealed connector 114 complete the necessary electrical circuit between the power unit 120 and the temperature control sensor 460. Instrumentation lines 435 and 436 complete a similar circuit for the temperature monitor sensor 462.

In one aspect of this embodiment, the heating element 150 is enclosed in a sleeve 470. In one embodiment, the sleeve 470 has a top portion 471 comprised of a polyester, such as a 1.2 oz. per square yard nonwoven polyester, and a bottom portion 472 comprised of an insulation layer, such as a 0.20 inch thick layer of silicone base foam, for reflecting heat upward toward the top surface 444. The bottom portion 472 can optionally include a woven fiberglass fabric laminated to the side next to the heating element 150. The seam between the top and bottom portions 471 and 472 of the sleeve 470 is sealed, such as by ultrasonic welding. In one aspect of this embodiment, the bottom portion 472 can be comprised of BISCO BF-1000 or BISCO IF-200 foam sheeting provided by the Rogers Corporation of Elk Grove, Ill.

A reflective or insulative material 473, such as heat-reflecting ethylene film, aluminized Mylar, or a silicone foam layer, can also be positioned adjacent to a lower surface 445 of the lower foam pad 142 for reflecting heat back into the heating pad 110 and to prevent it from escaping and being wasted. Accordingly, the term "layer" as used here could be a reflective coating applied to a surface of an existing structure, or it could be a separate layer of material having reflective qualities. An inner cover 490 neatly encloses the upper and lower foam pads 140 and 142 between the foam pads and the cover 112. In one embodiment, the inner cover 490 is a fire barrier material comprising a glass fiber strand encased in an acrylic sleeve. In one aspect of this embodiment, the Integrity 30 product made of a Modacrylic fiber knit and provided by Ventex, Inc. of Great Falls, Va., can be used for the inner cover 490. In other embodiments, other materials, both flame resistant and non-flame resistant, can be used for the inner cover 490. In yet other embodiments, the inner cover 490 can be omitted.

The form-fitting cover 112 is shaped and sized to neatly enclose the aforementioned components of the heating pad 110 and provide a durable exterior surface. In one embodiment, the sealed connector 114 provides a functional path through the cover 112 while providing a hermetic and antimicrobial, or "environmental," seal that prevents ingress of harmful or contaminating substances. The utility cord 130 sealably connects to the sealed connector 114 thereby connecting the power unit 120 to the temperature sensors 460 and 462 and the heating element 150. As explained above, venting of the heating pad 110 is provided by the vent tube 190 that passes through the sealed connector 114 and allows the heating pad 110 to vent into the power unit 120 via the utility cord 130.

In alternate embodiments, the cover 112 and the connector 114 can be configured to provide less than a hermetic or antimicrobial seal around the internal components of the heating pad 110. For example, in one alternate embodiment, the cover is a general purpose cover that, while generally covering at least a portion of the upper and lower foam pads 140 and 142, it does not provide a waterproof, hermetic, or antimicrobial seal. In one aspect of this alternate embodiment, all or a portion of the heating pad may be disposable in the event the general purpose cover is breached by a contaminating substance, such as moisture.

In one aspect of this embodiment, the upper foam pad 140 is comprised of a "slow recovery" foam, such as viscoelastic foam having an approximate indention force deflection (IFD) rating of 20 and a density of 4 lb. per cubic foot. This foam is thermally conductive and selected to efficiently transfer heat from the heating element 150 to a patient (not shown) positioned on top of the heating pad 110. This foam also demonstrates favorable compression characteristics resulting in evenly distributed patient support. In other embodiments, the upper foam pad 140 can be other viscoelastic foams having other IFD ratings and other densities. For example, the upper foam pad 140 can have an IFD rating of between 10 and 100 and have a density of between 0.5–8 lb. per cubic foot. In yet other embodiments, other foams can be selected for the upper foam pad 140 to satisfy other criteria. For example, an open cell foam can be selected to enhance convective heat transfer properties of the upper foam pad 140 when this attribute is desired. Conversely, a closed cell foam can be selected if it is desired to avoid fluid absorption. In yet another embodiment, a gel can be used in place of the upper foam pad 140. The upper foam pad 140 of the illustrated embodiment has a thickness dimension 446 of at least approximately 1.5 inches. In other embodiments, the dimension 446 can be between 0.25 inch and 3 inches, depending on the type of foam used, the heat output of the heating element 150, and the amount of compression desired. In yet other embodiments, the dimension 446 can have other values.

In another aspect of this embodiment, the lower foam pad 142 is comprised of a highly resiliency (HR) foam, such as 2.6 lb. per cubic foot foam with an approximate IFD rating of 34. This foam is selected because of its low thermal-conductive properties that insulate the heating element 150 and prevent heat from escaping through the bottom of the heating pad 110 and being wasted. In other embodiments, other foams can be selected for the lower foam pad 142 where other attributes are desired. For example, in one such embodiment, a foam having a density of between 0.5 and 8 lb. per cubic foot and an IFD rating of between 10 and 100 can be used. In yet other embodiments, a gel can be used for the lower foam pad 142. The lower foam pad 142 has a thickness dimension 447 that in the illustrated embodiment is at least approximately 2.5 inches. In other embodiments, the dimension 447 can be between 0.1 inch and 4 inches depending on the type of foam used and the amount of compression desired. In yet other embodiments, the dimension 447 can have other values, or the lower foam pad 142 can be omitted entirely. If the lower foam pad 142 is omitted in accordance with an embodiment, then support for a person (not shown) situated on the heating pad 110 is provided solely by the upper foam pad 140, and the upper foam pad should be sized accordingly.

In another aspect of this embodiment, the heating element 450 is a thermal-electric plastic, such as a carbon-filled plastic having copper braids for conducting AC or DC electrical current. For example, the thermal-electric plastic sold under the trade name StepWarmFloorEP30-3 or EP30-2 from Electro Plastics, Inc. of 4406 St. Vincent Ave., St. Louis, Mo. 63119, can be utilized in one embodiment. In other embodiments, other thermal-electric heating elements can be used. In yet other embodiments, heating elements other than thermal-electric heating elements can be used. For example, heating elements that circulate hot gas or hot water between the upper and lower foam pads 140 and 142 can be used in accordance with these embodiments.

The top portion 111 of the cover 112 of the illustrated embodiment is a urethane film laminated to a polyester/lycra knit substrate. This fabric features four-way stretch to prevent hammocking in the top surface and is also waterproof, flame-retardant, antimicrobial, and conductive to minimize the possibility of static electric discharges. The Penn Nyla company in England is one source for such material. The bottom portion 113 of the cover 112 of the illustrated embodiment is a conductive double-laminate vinyl with minimal stretch, such as provided by the Herculite Corporation. While exhibiting properties similar to the top portion 111, the bottom portion 113 is more durable than the top portion. The top and bottom portions 111 and 113 are constructed with welded sealed seams, such as by ultrasonic welding, to prevent fluid ingress and contamination. While not illustrated in FIG. 4, in alternate embodiments the top and bottom portions 111 and 113 can be joined together by a spiral zipper or similar attachment device. A separable cover such as this permits easy access to the internal components of the heating pad 110 for cleaning, repair, or replacement. In other embodiments, other mechanisms and methods can be used to join together the top and bottom portions 111 and 113 of the cover 112. For example, the top and bottom portions 111 and 113 can comprise edge flaps in one embodiment that can be sealably folded together to provide a simple attachment mechanism.

Figure 5:
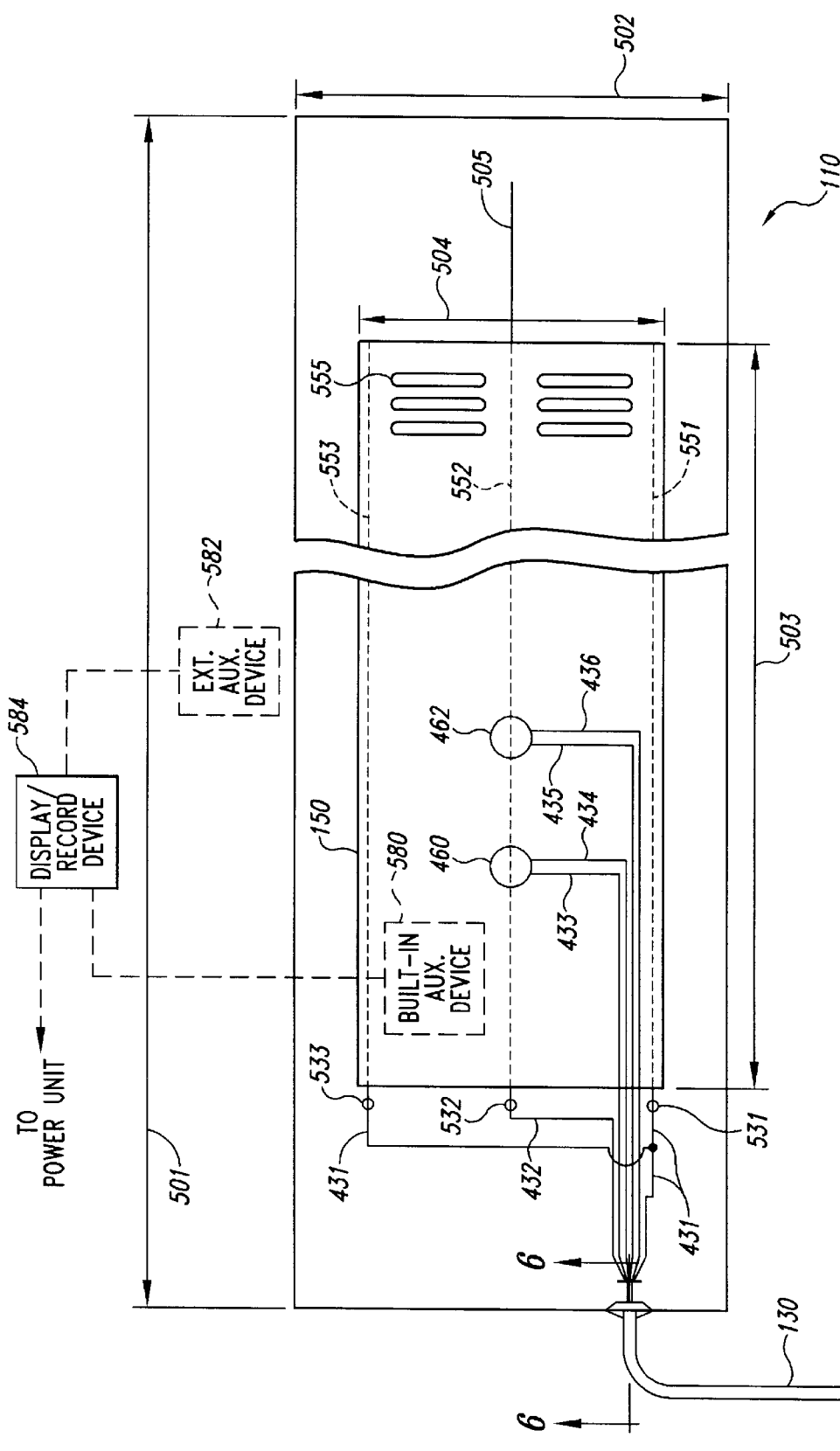
FIG. 5 is a schematic top cross-sectional view of a heating pad taken substantially along line 5—5 of FIG. 1 in accordance with an embodiment of the invention.

FIG. 5 is a schematic top cross-sectional view of a heating pad 110 taken substantially along line 5—5 of FIG. 1 in accordance with an embodiment of the invention. The heating pad 110 has a length dimension 501 and a width dimension 502. In one aspect of this embodiment, the length dimension 501 is approximately 80 inches and the width dimension 502 is approximately 20 inches. In other embodiments, these dimensions can have other values depending on the requirements of the particular application. For example, the width dimension 502 may be considerably larger than 20 inches to accommodate bariatric patients. In other applications, the length dimension 501 may be substantially less than 80 inches where, for example, only torso warming is desired. As will be readily apparent to those of ordinary skill in the relevant art, a heating pad in accordance with the present invention could have many shapes and sizes to meet the needs of a particular application. Round, curved, and multisegmented shapes, for example, are all possible and well within the scope of the present disclosure. In addition, to the extent that there are "standard" shapes for OR or Gurney pads, embodiments can be provided in these standard shapes. For example, if a universal stretcher pad is 24 inches wide by 76 inches long, then a heating pad in accordance with an embodiment can be provided with these dimensions.

The heating element 150 has a length dimension 503 and a width dimension 504. In one aspect of this embodiment, the length dimension 503 is 60 inches and the width dimension 504 is 14 inches. In other embodiments, the heating element can have other dimensions. In the illustrated embodiment, the heating element 150 is substantially centered relative to the dimensions of the heating pad 110. In other embodiments, the heating element 150 can be positioned in other locations depending on the particular heating characteristics sought.

In the illustrated embodiment, the heating element 150 has three copper braids 551, 552 and 553 extending longitudinally from one end of the heating element to the other. As is known, the copper braids 551–553 generate heat through electrical resistance while drawing relatively low current. The carbon-filled plastic of the heating element 150 suspends the copper braids 551–553 and is electrically resistive such that when an electrical charge is placed on adjacent copper braids, the carbon-filled plastic completes the electrical circuit between the two braids and generates heat, warming the heating element. One benefit of using carbon-filled plastic is that it is radiolucent. Thus, a patient can be X-rayed while situated on the heating pad 110, thereby avoiding time-consuming and potentially hazardous moving operations. Elongate holes 555 are positioned in equally spaced patterns in between the braids 551 and 552, and 552 and 553, of the heating element 150 to enhance flexibility of the heating element. In alternate embodiments, heating elements with more or fewer copper braids, with copper braids extending in different directions, and with more or fewer holes of different shapes and patterns can be used in a heating pad in accordance with alternate embodiments of the present invention.

As best seen by reference to FIG. 5, the sealed connector 114 is positioned to one side of the heating pad 110 away from a centerline 505 to avoid a patient's head (not shown, but presumably located toward the centerline) being in close proximity to the sealed connector. The power line 431 extends from the sealed connector 114 and branches to electrical leads 531 and 533 on the copper braids 551 and 553, respectively. The power line 432, in turn, extends from the sealed connector 114 to the lead 532 on the copper braid 552. The power lines 431 and 432 complete the necessary electrical circuit to the heating element 150. As explained above, the instrumentation lines 433 and 434 extend from the sealed connector 114 to the temperature control sensor 460. Similarly, the instrumentation lines 435 and 436 extend from the sealed connector 114 to the temperature monitor sensor 462. The temperature control sensor 460 and the temperature monitor sensor 462 are positioned in the upper foam pad 440 to optimize their ability to measure the true temperature of the heating pad 110 adjacent to a patient (not shown) positioned on the pad. Consistent with this objective, in the illustrated embodiment the temperature sensors 460 and 462 are positioned in the upper foam pad 140 approximately aligned with the centerline 505. This placement is intended to position the temperature sensors 460 and 462 in close proximity to the torso of a patient residing on the heating pad 110. In other embodiments, the placement of the temperature sensors can vary as required by the particular application.

Figure 6:
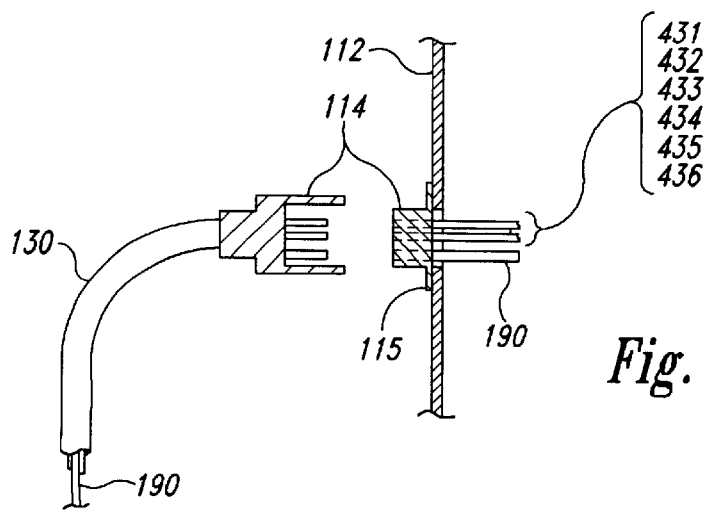
FIG. 6 is an enlarged schematic cross-sectional view of a sealed connector taken substantially along line 6—6 of FIG. 5 in accordance with an embodiment of the invention.

FIG. 6 is an enlarged schematic cross-sectional view of the sealed connector 114 taken substantially along line 6—6 of FIG. 5 in accordance with an embodiment of the invention. The sealed connector 114 of the illustrated embodiment is continuously secured or bonded to the cover 112 around an outer perimeter 115. In one embodiment, the sealed connector 114 is a bayonet locking DIN international connector with a gasket for providing liquid resistance. In one aspect of this embodiment, the sealed connector 114 will be a five pin type. In another aspect of this embodiment, the vent tube 190 can be incorporated into or adjacent to the connector to vent the interior of the heating pad 110 (not shown). Accordingly, the sealed connector 114 can provide a hermetic and antimicrobial seal between the inside and the outside of the heating pad 110. In other embodiments, the sealed connector 114 can utilize a conventional tortuous-path type seal.

Figure 7:
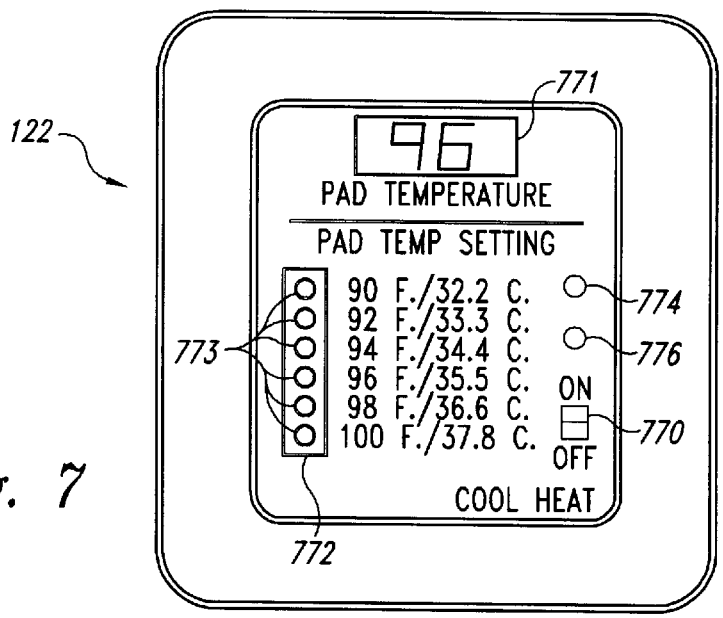
FIG. 7 is a schematic top view of a power unit control panel taken substantially along line 7—7 of FIG. 1 in accordance with an embodiment of the invention.

FIG. 7 is a schematic top view of the control panel 122 taken substantially along line 7—7 of FIG. 1 in accordance with an embodiment of the invention. Although the discussion that follows describes the control panel 122, the control panels 222 and 322 are substantially similar except as noted below. The control panel 122 includes an on/off switch 770, a temperature display 771, a temperature selection console 772, a power-loss warning light 774, and a circuit reset switch 776. The on/off switch 770 of the illustrated embodiment is a typical hospital grade rocker switch; however, various other types of on/off switches can also be used for this device. In an alternate embodiment, the on/off switch 770 can be omitted. In this alternate embodiment, the heating pad 110 begins warming to a selected temperature as soon as the power unit 120 is plugged in to a suitable AC outlet. Because the heating pad 110 requires little power, the omission of an on/off switch should not result in an appreciable expense.

In one aspect of this embodiment, the temperature display 771 is a digital LED display that indicates the current pad temperature as measured by the temperature monitor sensor 462 (not shown). The temperature display 771 is shaped and sized to enhance its readability by personnel working around the heating pad system 100 (also not shown). The temperature selection console 772 includes a plurality of selector buttons 773 associated with different temperature settings. In the illustrated embodiment, the available temperatures range from 90° F. to 100° F. in two-degree increments. As will be apparent to those of ordinary skill in the relevant art, other temperature ranges can be adopted depending on the requirements of the particular application. The desired temperature is selected by pressing the corresponding button after the on/off switch 770 has been switched to the on position. In another embodiment, the temperature selection is automatically set to a default temperature when the power unit is first turned on. In this embodiment, the preset default temperature can be the lowest available pad temperature.

In one embodiment, the power-loss warning light 774 provides an indication, such as by illuminating, when the power unit is on. For example, for those power units that do not have an internal power source, such as the power unit 120 of FIG. 1, if the light is on, the unit is powered-up. On those power units that do have their own internal power source, however, such as the power units 220 and 320 shown in FIGS. 2 and 3, the power-loss warning light 774 can, in one embodiment, flash or otherwise change its appearance to indicate when the internal power source is approaching a level that may compromise the continued performance of the heating pad. This compromising level, in one embodiment, can correspond to when only enough power remains in the internal power source to operate the heating pad at its highest temperature setting for one hour or less. In other embodiments as explained above, other types of warning devices can be incorporated to alert the user of low power levels. One such device is an audio warning device. Another such device is an internal power level digital display, similar to the temperature display 771, that digitally displays estimated available operating time remaining in hours.

The reset switch 776 is provided on the control panel 122 to permit a user to reset the power circuit after one or more safety fuses have been tripped. As will be explained in greater detail below, the power units 120, 220, and 320 of FIGS. 1–3, respectively, each include a number of safety fuses to avoid electrically overloading their respective heating pads or their circuitry. Those of ordinary skill in the relevant art will recognize that the control panel 122 can include other features in addition to those shown in FIG. 7 without departing from the scope and intent of the present disclosure. For example, instead of having the temperature selection console 772 with a plurality of selector buttons 773, the control panel could include a rotatable dial for selecting any temperature within a preselected range. In another embodiment, temperature selection could be accomplished using a touch screen having an up-arrow and a down-arrow. Any temperature within a preselected range could be selected in this embodiment by pressing the corresponding up- or down-arrow to accordingly raise or lower the pad temperature.

Figure 8:
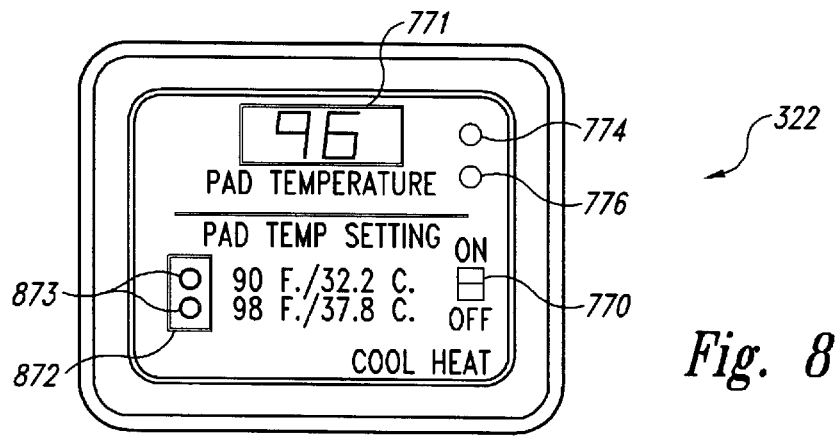
FIG. 8 is a schematic side elevational view of a power unit control panel taken substantially along line 8—8 of FIG. 3 in accordance with an embodiment of the invention.

FIG. 8 is a schematic side elevational view of the control panel 322 taken substantially along line 8—8 of FIG. 3 in accordance with an embodiment of the invention. The control panel 322 of the illustrated embodiment is substantially similar to the control panels 122 and 222 discussed above in accordance with FIG. 7. In one aspect of this embodiment, however, the control panel 322 includes a reduced set of dedicated temperature selector buttons 873 on a temperature selection console 872. The reduction in available temperature settings allows a lower profile control panel 322 that facilitates storage of the power unit 320 under the mobile support structure 302 as shown in FIG. 3. This reduction in available temperatures may not impair the utility of the heating pad system 300 (FIG. 3) because fewer temperature selections may be sufficient in patient transport applications. In alternate embodiments, the control panel 322 can include a wider range of available temperatures. For example, the control panel 322 in one alternate embodiment could include all the temperatures included on the control panels 122 and 222 discussed above in accordance with FIG. 7.

Figure 9:
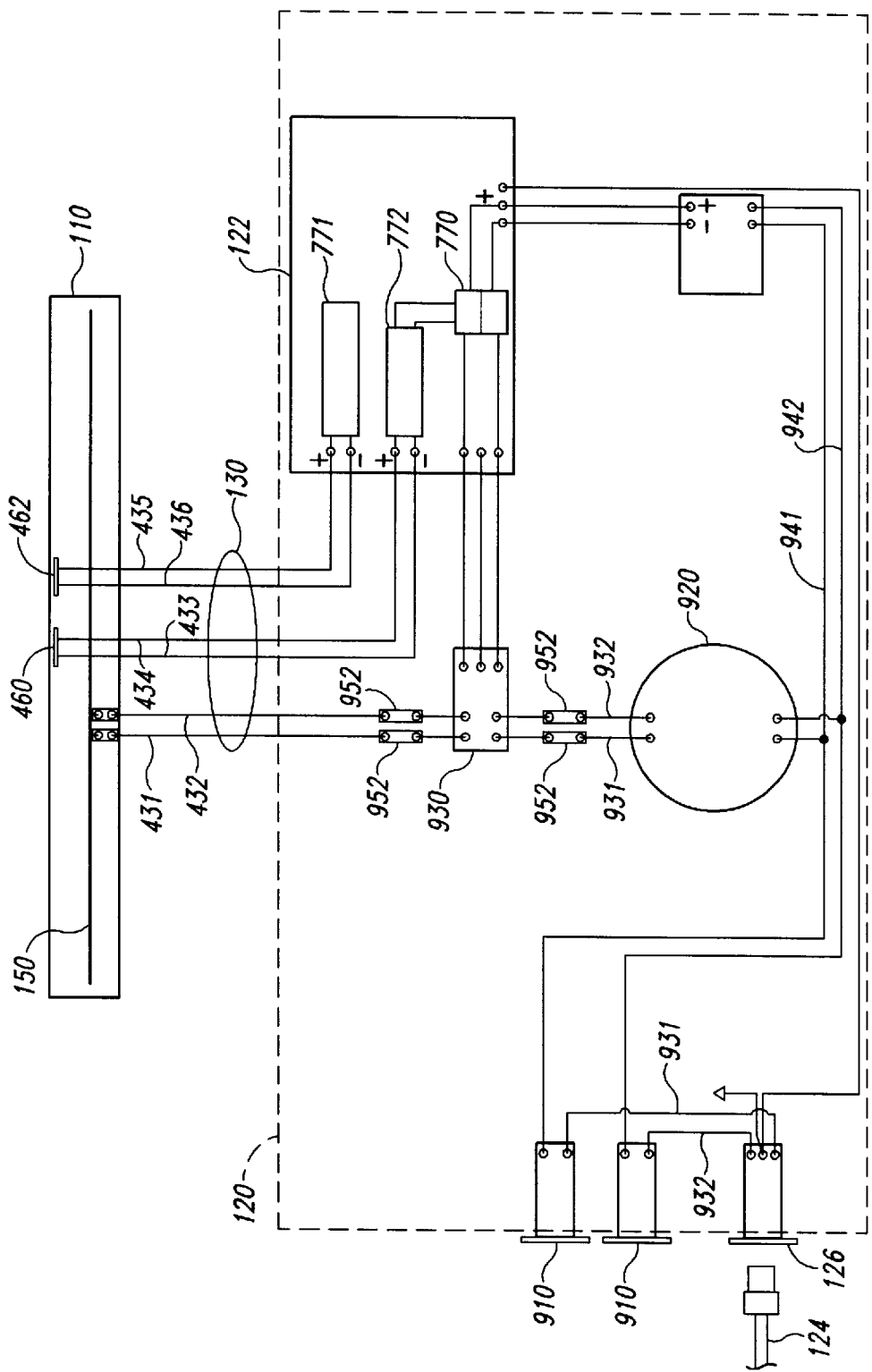
FIG. 9 is a schematic diagram of the power unit and heating pad of the heating pad system of FIG. 1 in accordance with an embodiment of the invention.

FIG. 9 is a schematic diagram of the power unit 120 and the heating pad 110 of FIG. 1 in accordance with an embodiment of the invention. The power unit 120 includes the receptacle 126, fuse holders 910 for fuses, a transformer 920, a relay 930, and the control panel 122. The retractable power cord 124 is received in the receptacle 126 to introduce power to the power unit 120. Power lines 931 and 932 extend from the receptacle 126 across the fuse holders 910 to the transformer 920. Power lines 941 and 942 branch off the power lines 931 and 932, respectively, and continue beyond the transformer 920 to provide power to the control panel 122. In one embodiment, the transformer 920 converts standard AC voltage from a hospital facility outlet to 24 volts DC. From the transformer 920 the power lines 931 and 932 proceed via a relay 930 to the heating element 150 in the heating pad 110. In one aspect of this embodiment, in-line fuses 952 can be employed to avoid electrical overload of the circuit. The relay 930 is controlled by the on/off switch 770 on the control panel 122. Accordingly, the on/off switch must be in the "ON" position before power is allowed to flow from the transformer 920 to the heating element 150.

As explained above, the instrumentation lines 433 and 434 connect the temperature control sensor 460 to the temperature selection console 772. Accordingly, the temperature control sensor 460 measures a temperature in the heating pad 110 and transmits this information (for example, as a varying voltage signal) to the temperature selection console 772. If the measured temperature exceeds a selected temperature (for example, the varying voltage signal exceeds a preset voltage), then the temperature selection console 772 opens the relay 930, which cuts off power to the heating element 150 thereby stopping heating of the heating pad 110 accordingly. Conversely, if the measured temperature is less than the selected temperature, then the temperature selection console 772 maintains the relay 930 in the closed position to continue warming the heating pad 110. As explained above, the temperature monitor sensor 462 is operably connected to the temperature display 771 on the control panel 122 by instrumentation lines 435 and 436. Accordingly, the temperature monitor sensor 462 measures a temperature of the heating pad 110 and transmits this information to the temperature display 771 where the measured temperature is digitally displayed.

Figure 10:
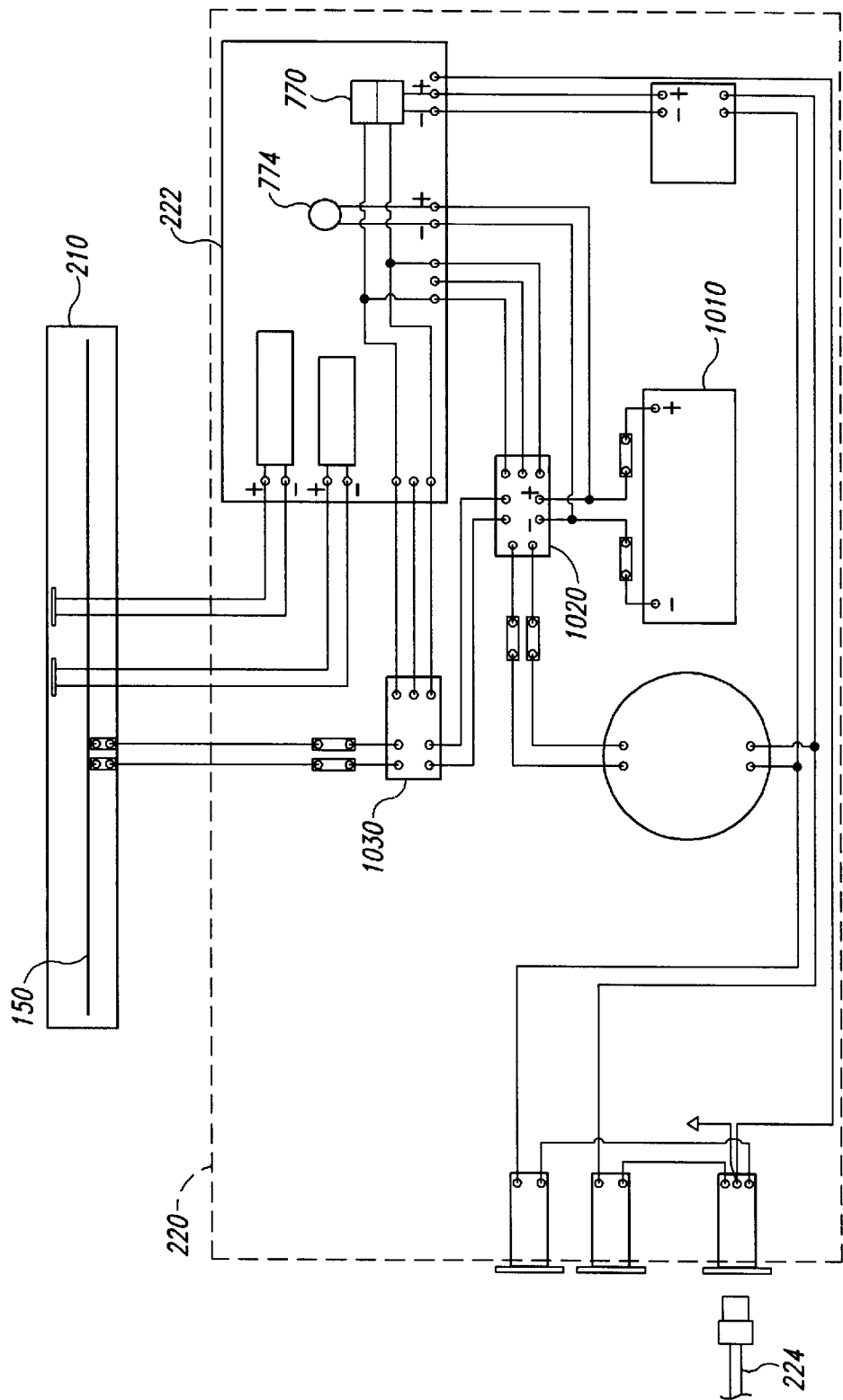
FIG. 10 is a schematic diagram of the power unit and heating pad of the heating pad system of FIG. 2 in accordance with an embodiment of the invention.

FIG. 10 is a schematic diagram of the power unit 220 and the heating pad 210 of FIG. 2 in accordance with an embodiment of the invention. The power and instrumentation systems of the power unit 220 are substantially similar to their counterparts in the power unit 120 discussed above in accordance with FIG. 9. The power unit 220, however, also includes an internal power source 1010 and an associated transfer relay/charger module 1020. In one aspect of this embodiment, the internal power source 1010 is a 24-volt DC battery pack. In other embodiments, other power sources can be used. As explained above, the internal power source 1010 enables the heating pad 210 to function independently of an external power source, allowing the heating pad system 200 to move freely outside the range of facility AC electrical outlets.

The on/off switch 770 controls the transfer relay/charger module 1020 and the relay 1030. When the on/off switch 770 is in the "ON" position, the transfer relay/charger module 1020 permits power from the internal power source to flow to the heating element 150 via the relay 1030. If the retractable power cord 224 is connected to an external power source, such as a facility AC power outlet, then power will instead flow from the external source to the heating element 150. As explained above, the internal power source 1010 is operably connected to the power-loss warning light 774 to provide a visual indication of when the stored power is approaching a pre-selected low power level. If the retractable power cord 224 is connected to an external power source when the internal power source is below this pre-selected level, then the transfer relay/charger module 1020 will direct power from the external source to the internal power source 1010 to recharge the internal power source and maintain it at a pre-selected charged level.

Figure 11:
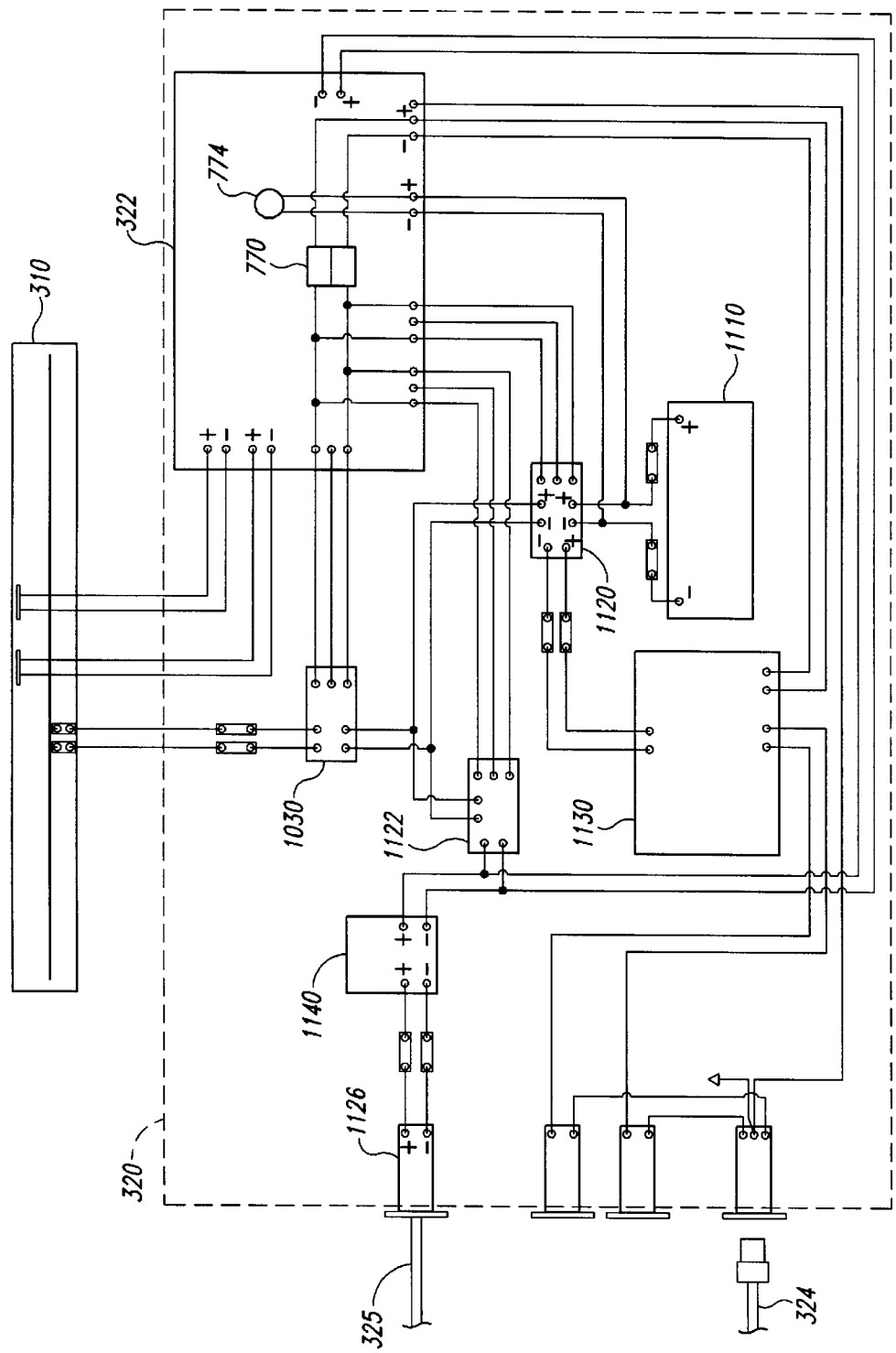
FIG. 11 is a schematic diagram of the power unit and heating pad of the heating pad system of FIG. 3 in accordance with an embodiment of the invention.

FIG. 11 is a schematic diagram of the power unit 320 and the heating pad 310 of FIG. 3 in accordance with an embodiment of the invention. The power unit 320 of the illustrated embodiment is substantially similar to the power unit 220 described above in accordance with FIG. 10, and includes an internal power source 1110. The power unit 320, however, also includes a receptacle 1126 for receiving the auxiliary power cord 325, a DC converter 1140, a switching power supply 1130, and a transfer relay 1122. The power unit 320 can utilize power from an external 12-volt DC power source through the auxiliary power cord 325, from an external AC power source through the retractable power cord 324, or from the internal power source 1110. When utilizing external AC power or internal power, the power unit 320 functions in a substantially similar manner as the power unit 220 described above in accordance with FIG. 10. When utilizing external power from a 12-volt DC power source, such as a 12-volt system on an ambulance vehicle, the power is converted to 24-volt DC power at the DC converter 1140. When the on/off switch 770 is switched to the "ON" position, the transfer relay 1122 permits power to flow from the DC converter 1140 to the heating pad 310 via a switching power supply 1130. The transfer relay 1122 also directs power through a transfer relay/charger module 1120 for recharging the internal power source 1110 if needed.

Referring to FIG. 5, those of ordinary skill in the relevant art will understand that various other apparatuses and functions relating to ascertaining, monitoring, and/or controlling the physical condition of a patient can be incorporated into the heating pad 110 in accordance with other embodiments of the invention. These other apparatuses can take the form of a built-in auxiliary device 580, or an external auxiliary device 582. In addition, output from these devices, and control input to these devices, can be implemented, displayed and/or recorded on a display/record device 584. The display/record device 584 can, in one embodiment, be connected to or otherwise incorporated with the power unit (not shown) for receiving power and/or data from the power unit.

The built-in auxiliary device 580 in one embodiment can be an instrumentation device, such as an additional temperature sensor, that is incorporated into the beating pad 110 for determining the body temperature of a patient placed on the heating pad. In one aspect of this embodiment, the additional temperature sensor can be exposed on an upper surface of the cover 112. Similarly, the display/record device 584 in one embodiment can be a suitable computer or microprocessor operably coupled to the additional temperature sensor for displaying the temperature on a suitable display. A data feedback loop between the additional temperature sensor and the suitable computer can also be utilized to control the temperature of the heating pad 110 according to the temperature of the patient as determined by the temperature sensor.

In another embodiment, the built-in auxiliary device 580 can be one or more moisture sensors incorporated into the cover 112 of the heating pad 110 to detect the presence of moisture on the surface of the heating pad. These moisture sensors can be connected to the display/record device 584 to provide a signal if, and when, moisture is present on the cover 112. This signal can be used to alert hospital personnel of unexpected leakage of medical or bodily fluids. In yet another embodiment, the built-in auxiliary device 580 can be an array of force sensors incorporated into the heating pad 110 so that the weight of a patient can be ascertained and monitored during the patient's period of care. A drop in body weight could be used to provide an indication of deteriorating physical condition. In yet another embodiment of the invention, the heating pad 110 can have a plurality of alternating pressure portions that exert a varying massage-like pressure against a patient situated on the pad. Additionally, provisions for electrically grounding a patient can be provided to avoid detrimental electrical interactions with the patient. For example, such grounding could be used to avoid electrically shocking the patient during medical procedures involving a cauterizing pencil.

From the foregoing, it will be appreciated by those of ordinary skill in the relevant art that various provisions for determining and monitoring the vital signs of a patient situated on the heating pad 110 can also be incorporated into the heating pad in accordance with additional embodiments of the invention. For example, in one embodiment the built-in auxiliary device 580 comprises exposed electrodes on the pad's upper surface that determines the heart rate of the patient. In another embodiment, the external auxiliary device 582 is comprised of electrode patches adhered to the patient's body to determine heart rate. In both these embodiments, the electrodes can be connected to the display/record device 584, such as an EKG, to graphically display and monitor the patient's heart rate. Similarly, blood pressure and respiratory functions can also be determined by incorporating devices well-known in the relevant art into the heating pad 110. These devices can be like the built-in auxiliary device 580, that are wholly integrated within the heating pad system 100 and are used to passively monitor the patient; or, these devices can be like the external auxiliary device 582, such as a blood pressure cuff, that appends from the heating pad and actively monitors the patient in the conventional manner.

In one aspect of these alternate embodiments, the heating pad system 100 can also include appropriate interface connections so that the external auxiliary device 582 and the display/record device 584, which are not part of the heating pad system per se, can be interfaced with the heating pad system. The display/record device 584 can be used to receive signals or data from the measurement devices incorporated into the heating pad 110, or to send control input to the heating element or the other built-in or external auxiliary devices. The heating pad system 100 can also be connected to the display/record device 584 so that various measurements of the patient's conditions can be ascertained and recorded over a period of time. In these alternate embodiments as discussed above, additional displays can be incorporated into the control panel 122 to display the corresponding measurements and data to a user of the heating pad system 100, such as hospital personnel. The foregoing discussion is equally applicable to the heating pad systems 100, 200 and 300 of FIGS. 1–3, respectively.

Figure 12:
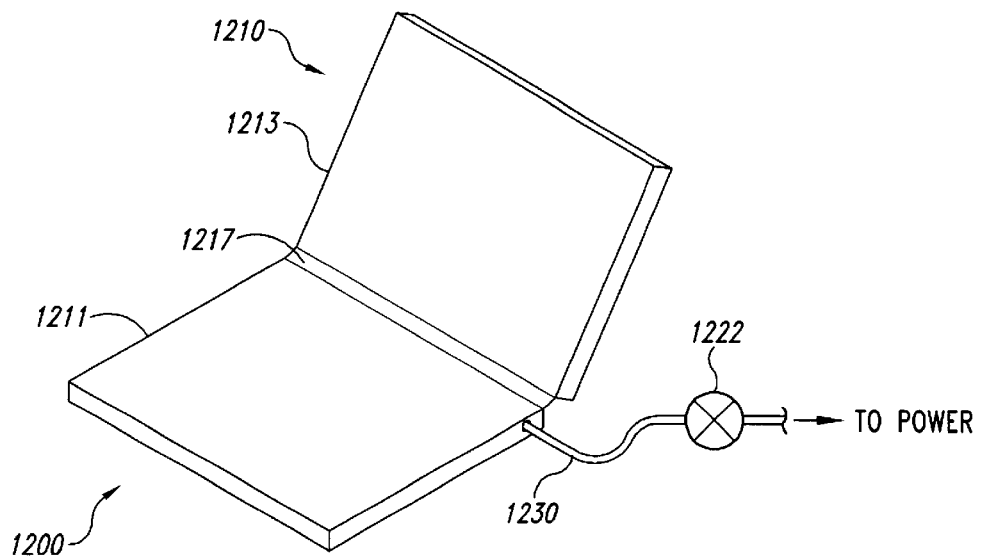
FIG. 12 is an isometric view of a heating pad system in accordance with an alternate embodiment of the invention.

FIG. 12 is an isometric view of a heating pad system 1200 in accordance with an alternate embodiment of the invention. The heating pad system 1200 of the illustrated embodiment is shaped and sized for use on a conventional chair or other seating device, and includes a first pad portion 1211 hingedly connected to a second pad portion 1213 by a flexible coupling 1217. A utility cord 1230 connects the heating pad system 1200 to a power source, and a temperature controller 1222 controls the temperature of the first and second pad portions 1211 and 1213. The first and second pad portions 1211 and 1213 are substantially similar in both structure and function as the first and second pad portions 111 and 113 of the heating pad system 100 shown in FIG. 1. In one aspect of this embodiment, however, the heating pad system 1200 does not include temperature sensors. In other embodiments, temperature sensors could be incorporated into the heating pad system 1200.

The heating pad system 1200 can be used in accordance with embodiments of the invention to provide personal warmth to a user seated on the first pad portion 1211 with his or her back against the second pad portion 1213. For example, in one embodiment the heating pad system 1200 can be used in this manner to provide warmth to a person undergoing kidney dialysis treatment. As is known, body temperature decline often accompanies kidney dialysis treatment as a result of treated blood re-entering the body at a temperature below normal body temperature. In other non-clinical embodiments, the heating pad system 1200 can be used to provide warmth during outdoor recreational activities in cold weather, such as watching a sports game or riding a chair lift at a ski resort.

Figure 13:
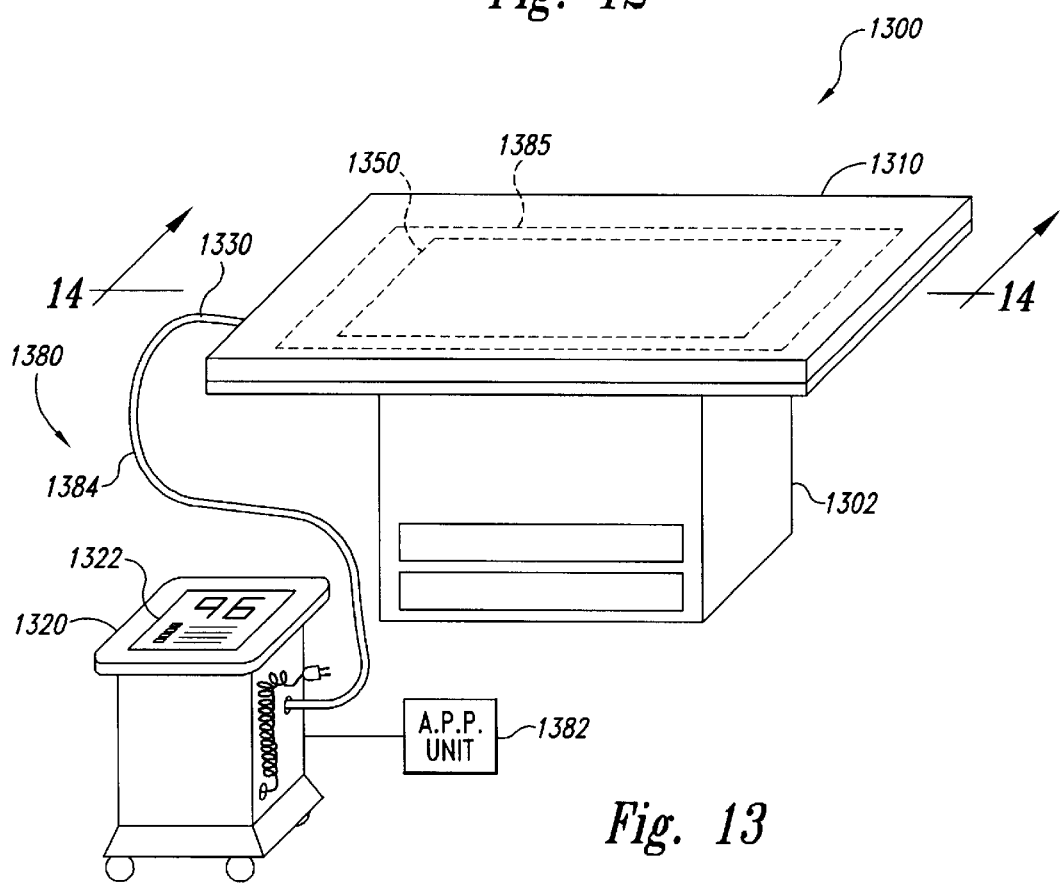
FIG. 13 is a schematic isometric view of a heating pad system that includes an alternating pressure pad in accordance with an embodiment of the invention.

FIG. 13 is a schematic isometric view of a heating pad system 1300 that includes an alternating pressure pad (APP) 1385 in accordance with an embodiment of the invention. The heating pad system 1300 of the illustrated embodiment is substantially similar to the heating pad system 100 of FIG. 1, and includes a rectangular-shaped heating pad 1310 that includes a heating element 1350 positioned beneath the APP 1385. The heating pad system 1310 is positioned on a stationary support structure 1302, such as a conventional OR table. The heating pad system 1300 also includes a power unit 1320 that is substantially similar to the power unit 120 of FIG. 1; however, the power unit 1320 also includes an APP pump unit 1382, such as a four-channel APP pump unit, for providing pressurized air through ducting 1384 to the APP 1385. The ducting 1384 is incorporated into a utility cord 1330 that in all other respects is substantially similar to the utility cord 130 of FIG. 1.

The heating pad system 1300 functions in a substantially similar manner as the heating pad system 100 of FIG. 1 with the exception of the APP 1385. As is known, bedsores are a result of patients spending extended periods of time in one position so that localized pressure points supporting their body weight lead to internal bruising. The possibility of bedsores occurring in this manner also exists for anesthetized patients during prolonged surgical procedures. APP pads are known devices that seek to prevent bedsores by alternating pressure to adjacent portions, or channels, of a pressurized pad so as to alternate the areas of support under a patient. In one embodiment, a four-channel APP will alternate pressure to adjacent pressure channels once every five minutes. In other embodiments, other more or fewer channels or other time periods can be used. One advantage of the heating pad system 1300 is that the integration of the APP into the heating pad system adds a further measure of prevention against bedsores that is not offered by conventional patient-warming devices.

Figure 14:
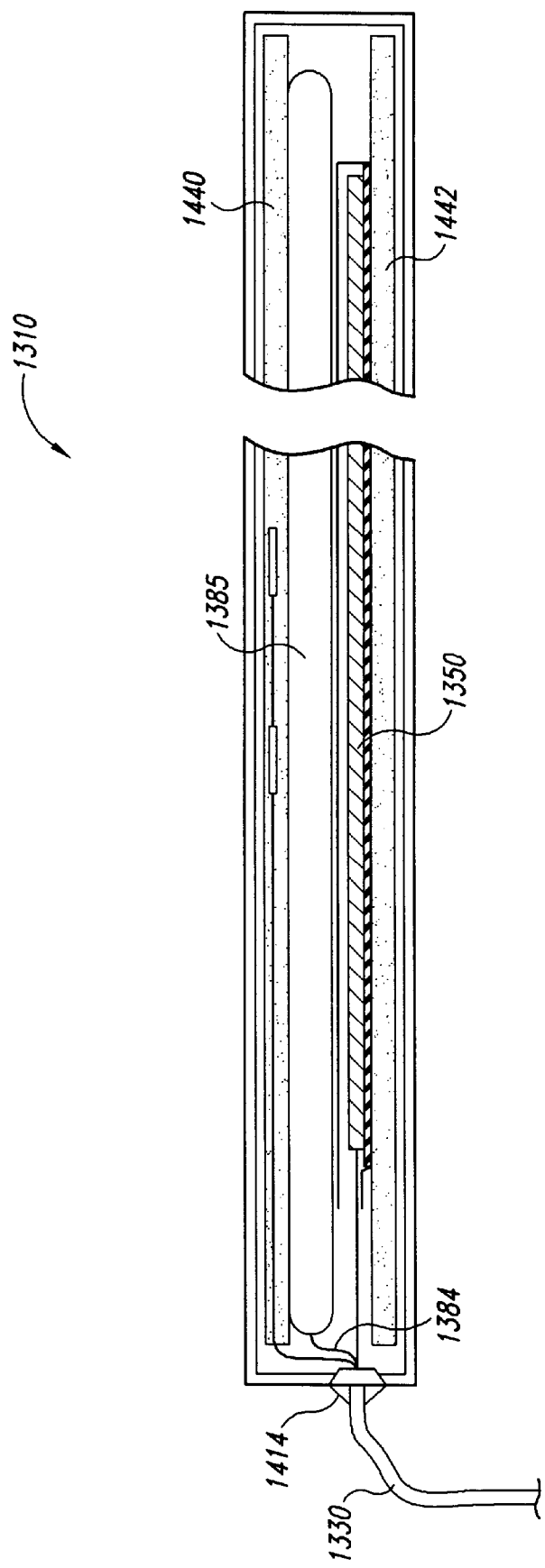
FIG. 14 is an enlarged schematic side cross-sectional view of a heating pad that includes an alternating pressure pad taken substantially along line 14—14 of FIG. 13 in accordance with an embodiment of the invention.

FIG. 14 is an enlarged schematic side cross-sectional view of the heating pad 1310 taken substantially along line 14—14 of FIG. 13 in accordance with an embodiment of the invention. As explained above, the heating pad 1310 is substantially similar to the heating pad 110 of FIG. 1 (shown in cross-sectional view in FIG. 4) with some notable exceptions resulting from the inclusion of the APP 1385. For example, the heating pad 1310 includes a sealed connector 1414 that is substantially similar to the sealed connector 114 of FIG. 1. The sealed connector 1414, however, also sealably receives the ducting 1384 from the APP pump unit 1382 (not shown). The ducting 1384 then extends from the sealed connector 1414 to the APP 1385 to provide the necessary alternating pressure pulses to the APP.

Because of the added thickness of the APP 1385, the heating pad 1310 includes an upper foam pad 1440 and a lower foam pad 1442 that are considerably thinner than their counterparts 140 and 142, respectively, in the heating pad 110 of FIG. 1. For example, the upper foam pad 1440 of this embodiment is approximately 0.38 inch thick, while the lower foam pad 1442 is approximately 0.50 inch thick. In another aspect of this embodiment, the upper foam pad 1440 can have an IFD of 20 while the lower foam pad has an IFD of 60. In other embodiments, other thicknesses and other IFDs can be used. The heating element 1350 and the other components of the heating pad 1310 are substantially similar to their counterparts in the heating pad 110 of FIG. 1, and further description is accordingly not required here.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," and words of similar import, when used in this application, shall refer to this application as a whole and not to any particular portions of this application.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings of the invention provided herein can be applied to other heating pad systems, not only to the embodiments described above. In addition, all of the above references and U.S. patents and applications are incorporated herein by reference.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

From the foregoing, it will be appreciated that even though specific embodiments of the invention have been described herein for purposes of illustration, a myriad other configurations and uses exist for heating pad systems in accordance with the present disclosure. It will also be appreciated that various modifications may be made to the embodiments described herein without deviating from the spirit or scope of the present disclosure. In general, in the following claims, the terms used should not be construed to limit the invention to the specific embodiments disclosed in the specification and the claims, but should be construed to include all heating pad systems that operate under the claims. Accordingly, the invention is not limited by the disclosure, but instead the scope of the invention is to be determined entirely by the claims.

We claim:

1. A heating pad system useable for warming a person on a support structure, the heating pad system comprising:
    a heating pad positionable on the support structure, the heating pad including:
        a thermal-electric heating element;
        a sleeve enclosing at least a portion of the thermal-electric heating element, wherein the sleeve has a top portion comprising polyester and a bottom portion comprising an insulation layer;
        an upper foam pad; and
        a lower foam pad, the upper and lower foam pads sandwiching at least a portion of the sleeve and the thermal-electric heating element; and
    a power unit configured to provide electrical power to the thermal-electric heating element, the power unit including a control panel having at least one temperature selector, the temperature selector for selecting at least one heating pad temperature.

2. The heating pad system of claim 1 wherein the support structure is an operating room table.

3. The heating pad system of claim 1 wherein the heating pad further includes a cover enclosing at least a portion of the upper and lower foam pads and the thermal-electric heating element.

4. The heating pad system of claim 1 wherein the heating pad further includes:
    a cover enclosing at least a portion of the upper and lower foam pads and the thermal-electric heating element; and
    a sealed connector secured to the cover, the power unit providing electrical power to the thermal-electric heating element via a utility cord connected to the sealed connector.

5. The heating pad system of claim 1 wherein the thermal-electric heating element is a first thermal-electric heating element, wherein the heating pad is a first heating pad, and wherein the heating pad system further comprises:
    a second heating pad, the second heating pad including a second thermal-electric heating element; and
    a flexible coupling, the flexible coupling providing a hinge-like connection between the first heating pad and the second heating pad.

6. The heating pad system of claim 1 wherein the heating pad further includes a sheet of reflective material positioned adjacent to at least one of the upper foam pad and the lower foam pad.

7. The heating pad system of claim 1 wherein the heating pad further includes a reflective polyethylene material positioned adjacent to at least one of the upper foam pad and the lower foam pad.

8. The heating pad system of claim 1 wherein the heating pad further includes a temperature sensor for measuring heating pad temperatures, at least a portion of the temperature sensor being positioned at least proximate to the upper foam pad.

9. The heating pad system of claim 1 wherein the heating pad further includes a temperature sensor for measuring heating pad temperatures, at least a portion of the temperature sensor being positioned at least proximate to the upper foam pad, wherein the temperature sensor is operably connected to the power unit, and wherein the power unit further includes a temperature control circuit configured to control electrical power provided to the thermal-electric heating element based on a selected heating pad temperature and a measured heating pad temperature.

10. The heating pad system of claim 1 wherein the power unit further includes a temperature display for displaying heating pad temperatures.

11. The heating pad system of claim 1 wherein the power unit further includes a temperature display, and wherein the heating pad further includes a temperature sensor for providing heating pad temperatures to the temperature display.

12. The heating pad system of claim 1 wherein the power unit further includes a digital numeric temperature display for displaying heating pad temperatures.

13. The heating pad system of claim 1 wherein the power unit further includes a temperature display for displaying heating pad temperatures, and wherein the heating pad further includes a first temperature sensor and a second temperature sensor, the first temperature sensor being operably connected to the power unit, to control electrical power provided to the thermal-electric heating element, the second temperature sensor being operably connected to the power unit for providing measured heating pad temperatures to the temperature display.

14. The heating pad system of claim 1 wherein at least one of the upper foam pad and the lower foam pad comprises a viscoelastic foam.

15. The heating pad system of claim 1 wherein the thermal-electric heating element comprises a carbon-filled material.

16. The heating pad system of claim 1 wherein at least one of the upper foam pad and the lower foam pad comprises a slow-recovery viscoelastic foam.

17. The heating pad system of claim 1 wherein the thermal-electric heating element comprises one or more copper elements for generating heat.

18. The heating pad system of claim 1 wherein the thermal-electric heating element is comprised of three longitudinally oriented copper braids suspended in a carbon-filled plastic, the carbon-filled plastic being at least substantially radiolucent.

19. The heating pad system of claim 1, wherein the heating pad further includes an alternating pressure pad positioned adjacent to the thermal-electric heating element.

20. The heating pad system of claim 1 wherein the heating pad includes an alternating pressure pad positioned between the upper and lower foam pads.

21. The heating pad system of claim 1, further comprising:
a temperature sensor configured to determine a temperature of the person on the support structure; and
a display device operably connected to the temperature sensor and configured to display the temperature of the person.

22. The heating pad system of claim 1 wherein the heating pad further includes a moisture sensor configured to determine the presence of moisture at least proximate to the heating pad.

23. The heating pad system of claim 1, further comprising:
a blood pressure cuff configured to be releasably attached to the person on the support structure for determining the blood pressure of the person; and
a display device operably connected to the blood pressure cuff and configured to display the blood pressure of the person on the support structure.

24. The heating pad system of claim 1, further comprising a grounding device configured to electrically ground the person on the support structure.

25. A heating pad system useable for warming a person on a mobile support structure, the heating pad system comprising:
a heating pad positionable on the mobile support structure, the heating pad including:
an upper foam pad;
a lower foam pad; and
a thermal-electric heating element sandwiched between the upper and lower foam pads; and
a power unit attachable to the mobile support structure, the power unit including:
a power source for providing electrical power to the thermal-electric heating element;
a side-facing first control panel facing a first direction, the first control panel having a first set of temperature selectors corresponding to a first set of heating pad temperatures; and
a side-facing second control panel facing a second direction, the second control panel having a second set of temperature selectors corresponding to a second set of heating pad temperatures.

26. The heating pad system of claim 25 wherein the mobile support structure is a gurney.

27. The heating pad system of claim 25 wherein the second direction is opposite to the first direction.

28. The heating pad system of claim 25 wherein the mobile support structure has a bed portion suitable for the person to lay on, and wherein the power unit is releasably attachable to the mobile support structure at least partially beneath the bed portion.

29. The heating pad system of claim 25 wherein the power unit is optionally connectable to an AC power source, wherein when the power unit is connected to the AC power source the power unit can provide electrical power to the thermal-electric heating element from the AC power source.

30. The heating pad system of claim 25 wherein the power unit is optionally connectable to a 12-volt DC power source, wherein when the power unit is connected to the 12-volt DC power source the power unit can provide electrical power to the thermal-electric heating element from the 12-volt DC power source.

31. The heating pad system of claim 25 wherein:
the power unit is optionally connectable to an AC power source, wherein when the power unit is connected to the AC power source the power unit can provide electrical power to the thermal-electric heating element from the AC power source; and wherein
the power unit is optionally connectable to a 12-volt DC power source, wherein when the power unit is connected to the 12-volt DC power source the power unit can provide electrical power to the thermal-electric heating element from the 12-volt DC power source.

32. The heating pad system of claim 25 wherein the heating pad further includes a cover at least partially enclosing the upper foam pad, the lower foam pad, and the thermal-electric heating element.

33. The heating pad system of claim 25 wherein the heating pad further includes reflective material positioned adjacent to the lower foam pad such that the lower foam pad is disposed between the sheet of reflective material and the thermal-electric heating element.

34. The heating pad system of claim 25 wherein the power unit includes a temperature display for displaying heating pad temperatures.

35. The heating pad system of claim 25 wherein at least the upper foam pad includes viscoelastic memory foam.

36. The heating pad system of claim 25 wherein the power unit further includes a power-loss indicator for indicating a status of the power source.

37. The heating pad system of claim 25 wherein the power unit further includes a power-loss indicator for indicating a status of the power source, the power-loss indicator including a visual indicator.

38. The heating pad system of claim 25 wherein the power unit further includes a power-loss indicator for indicating a status of the power source, the power-loss indicator including a visible light source.

39. The heating pad system of claim 25 wherein the power unit further includes a power-loss indicator for indicating a status of the power source, the power-loss indicator including a digital display.

40. The heating pad system of claim 25 wherein the power unit further includes an audio power-loss indicator for indicating a status of the power source.

41. A heating pad system useable for warming a person on a mobile support structure, the heating pad system comprising:
    a heating pad positionable on the mobile support structure, the heating pad including:
        an upper foam pad;
        a lower foam pad; and
        a thermal-electric heating element sandwiched between the upper and lower foam pads; and
    a power unit attachable to the mobile support structure, the power unit including:
        a power source for providing electrical power to the thermal-electric heating element;
        a side-facing first control panel facing a first direction, the first control panel having a set of temperature selectors corresponding to a set of heating pad temperatures; and
    a side-facing second control panel facing a second direction, the second control panel having the set of temperature selectors corresponding to the set of heating pad temperatures.

42. A heating pad system useable for warming a person on a mobile support structure, the heating pad system comprising:
    heating pad positionable on the mobile support structure, the heating pad including:
        an upper foam pad having an upper surface;
        a lower foam pad;
        a thermal-electric heating element sandwiched between the upper and lower foam pads;
        a first temperature sensor configured to measure heating pad temperatures, wherein at least a portion of the first temperature sensor is positioned adjacent to the upper surface of the upper foam pad; and
        a second temperature sensor configured to measure heating pad temperatures, wherein at least a portion of the second temperature sensor is positioned adjacent to the upper surface of the upper foam pad, and
    a power unit attachable to the mobile support structure, the power unit including:
        a power source for providing electrical power to the thermal-electric heating element;
        a control panel having at least one temperature selector, wherein the temperature selector is usable to select at least one heating pad temperature;
        a temperature control circuit coupled to the first temperature sensor to control electrical power provided to the thermal-electric heating element based on a selected heating pad temperature and a measured heating pad temperature; and
        a temperature display coupled to the second temperature sensor to display heating pad temperatures received from the second temperature sensor.

43. The heating pad system of claim 42 wherein at least one of the upper foam pad and the lower foam pad includes viscoelastic foam.

44. The heating pad system of claim 42 wherein the mobile support structure is a gurney.

45. The heating pad system of claim 42 wherein the mobile support structure is a hospital bed.

46. The heating pad system of claim 42 wherein the thermal-electric heating element is at least generally radiolucent.

47. The heating pad system of claim 42 wherein the mobile support structure is an operating room table that is a least partially mobile.

48. The heating pad system of claim 42 wherein the mobile support structure includes a bed portion suitable for the person to lay on, and wherein the power unit is releasably attachable to the mobile support structure at least partially beneath the bed portion.

49. The heating pad system of claim 42 wherein the power unit is optionally connectable to an AC power source, wherein when the power unit is connected to the AC power source the power unit can provide electrical power to the thermal-electric heating element from the AC power source.

50. The heating pad system of claim 42 wherein the control panel further includes a power-loss indicator for indicating a status of the power source.

51. A heating pad system useable for warming a person on a support structure, the heating pad system comprising:
    a heating pad positionable on the support structure, the heating pad including:
        a foam pad; and
        a thermal-electric heating element positioned at least proximate to the foam pad; and
    a power unit configured to provide electrical power to the thermal-electric heating element, the power unit including:
        a first control panel facing a first direction, the first control panel having at least a first temperature selector configured to control a first temperature of the heating pad; and
        a second control panel facing a second direction, the second control panel having at least a second temperature selector configured to control a second temperature of the heating pad.

52. The heating pad system of claim 51 wherein the first direction is at least generally opposite to the second direction.

53. The heating pad system of claim 51 wherein the support structure includes an operating room table.

54. The heating pad system of claim 51 wherein the first and second temperatures of the heating pad are at least generally the same.

55. The heating pad system of claim 51 wherein the first and second temperature selectors are configured to control the same temperature.

56. A heating pad system useable for warming a person on a support structure, the heating pad system comprising:
    a heating pad positionable on the support structure, the heating pad including:
        a foam pad; and
        a thermal-electric heating element positioned at least proximate to the foam pad; and a power unit configured to provide electrical power to the thermal-electric heating element, the power unit including:
- a first control panel facing a first direction, the first control panel having a first temperature display configured to display a first temperature of the heating pad; and
- a second control panel facing a second direction, the second control panel having a second temperature display configured to display a second temperature of the heating pad.

57. The heating pad system of claim 56 wherein the first direction is at least generally opposite to the second direction.

58. The heating pad system of claim 56 wherein the support structure includes an operating room table.

59. The heating pad system of claim 56 wherein the first and second temperatures of the heating pad are at least generally the same.

60. The heating pad system of claim 56 wherein the first and second temperature displays are configured to display the same temperature.

61. A heating pad system comprising:
- a heating pad, the heating pad including:
  - a foam pad;
  - a heating element positioned adjacent to the foam pad;
  - a first temperature sensor positioned at least proximate to the foam pad; and
  - a second temperature sensor positioned at least proximate to the foam pad, and
- a power unit configured to provide power to the heating element, the power unit including:
  - a temperature control circuit coupled to the first temperature sensor, wherein the temperature control circuit is configured to control electrical power provided to the heating element; and
  - a temperature display coupled to the second temperature sensor, wherein the temperature display is configured to display heating pad temperatures.

62. The heating pad system of claim 61 wherein the temperature control circuit is configured to control electrical power provided to the heating element based on a selected heating pad temperature and a measured heating pad temperature.

63. The heating pad system of claim 61 wherein the temperature display is configured to display heating pad temperatures received from the second temperature sensor.

64. The heating pad system of claim 61 wherein the heating element is a thermal-electric heating element.

65. The heating pad system of claim 61 wherein the heating element is at least generally radiolucent.

* * * * *

UNITED STATES PATENT AND TRADEMARK OFFICE
CERTIFICATE OF CORRECTION

PATENT NO. : 6,653,607 B2
DATED : November 25, 2003
INVENTOR(S) : Kent Douglas Ellis et al.

It is certified that error appears in the above-identified patent and that said Letters Patent is hereby corrected as shown below:

<u>Title page,</u>
Item [57], ABSTRACT,
Line 1, delete "is" between "system" and "useable";

<u>Column 5,</u>
Line 59, "beating pad" should be -- heating pad --;

<u>Column 14,</u>
Line 60, "beating pad" should be -- heating pad --.

Signed and Sealed this

Tenth Day of February, 2004

JON W. DUDAS
*Acting Director of the United States Patent and Trademark Office*